United States Patent [19]

Lewin et al.

[11] 4,015,939

[45] Apr. 5, 1977

[54] COMPETITIVE BINDING THYROID ASSAY WITH IMPROVED BOUND-FREE SEPARATION STEP

[75] Inventors: Nathan Lewin, Corte Madera; Vito J. Mangiardi, San Rafael, both of Calif.

[73] Assignee: Bio-Rad Laboratories, Inc., Richmond, Calif.

[22] Filed: May 12, 1976

[21] Appl. No.: 685,595

[52] U.S. Cl. .................. 23/230 B; 23/230.3; 23/230.6; 260/9

[51] Int. Cl.² ...................................... G01N 33/16

[58] Field of Search ........... 23/230 B, 230.3, 230.6; 210/DIG. 23; 424/1, 1.5; 250/303, 304; 260/2.1 R, 9

[56] References Cited

UNITED STATES PATENTS

| | | | |
|---|---|---|---|
| 3,516,794 | 6/1970 | Murty et al. | 23/230 B |
| 3,702,821 | 11/1972 | Fernandez | 23/230 B X |
| 3,721,528 | 3/1973 | Mead et al. | 23/230 B |
| 3,743,482 | 7/1973 | Eisentraut | 23/230.6 |
| 3,784,489 | 1/1974 | Dales et al. | 260/2.1 R X |
| 3,823,001 | 7/1974 | Zabin | 23/230 B |
| 3,929,981 | 12/1975 | Murty et al. | 23/230 B X |

*Primary Examiner*—Joseph Scovronek
*Attorney, Agent, or Firm*—Townsend and Townsend

[57] ABSTRACT

Improved competitive binding thyroid hormone assay in which thyroid hormone bound by thyroid binding protein is separated from free thyroid hormone by removal with an intermediate base anion exchange resin. Typical are resins characterized by having an aliphatic lattice, particularly, a polyalkyleneamine lattice having tertiary and quaternary amine groups. The resin is advantageously added for the separation function in tablet form.

10 Claims, 2 Drawing Figures

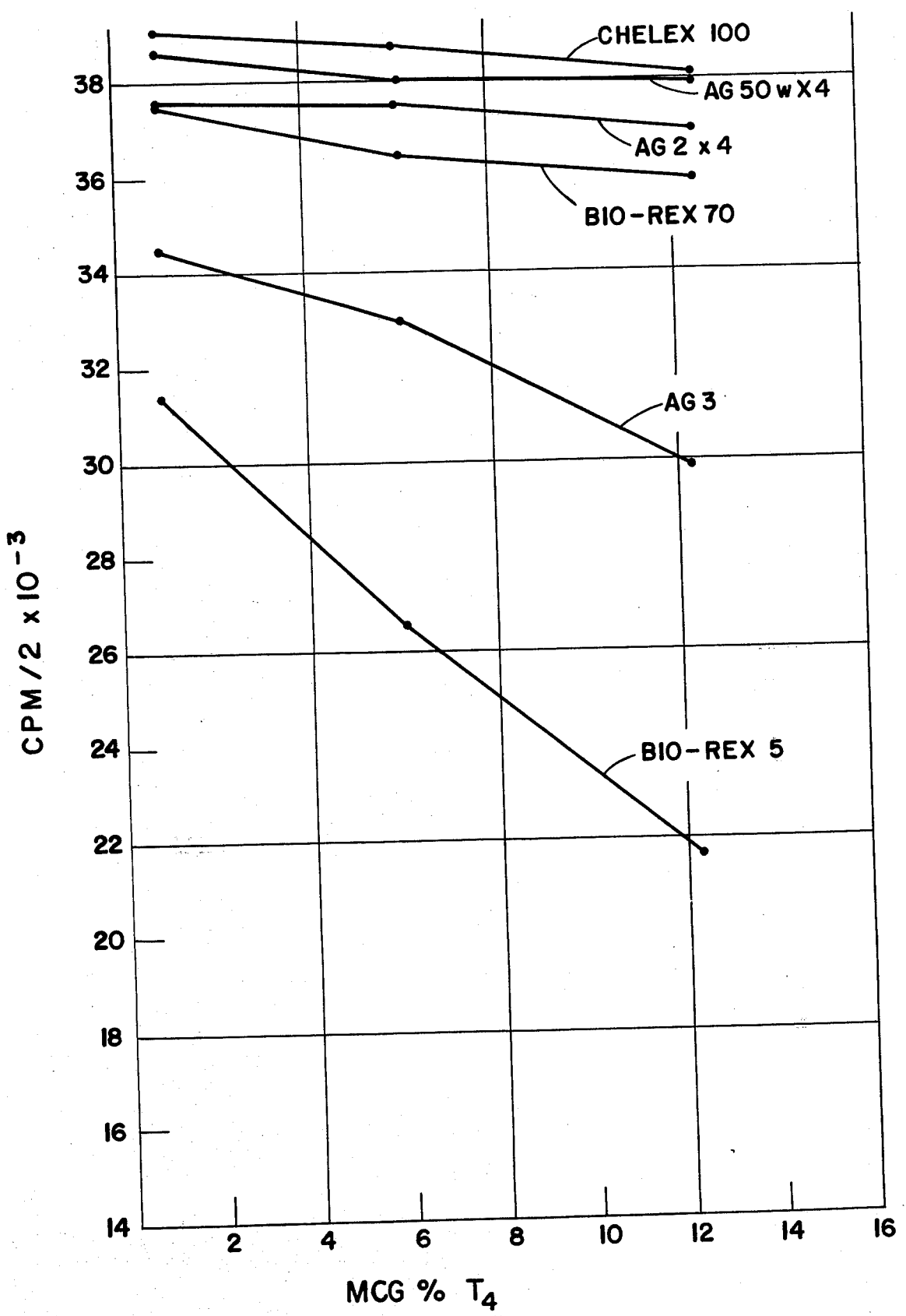
FIG_1

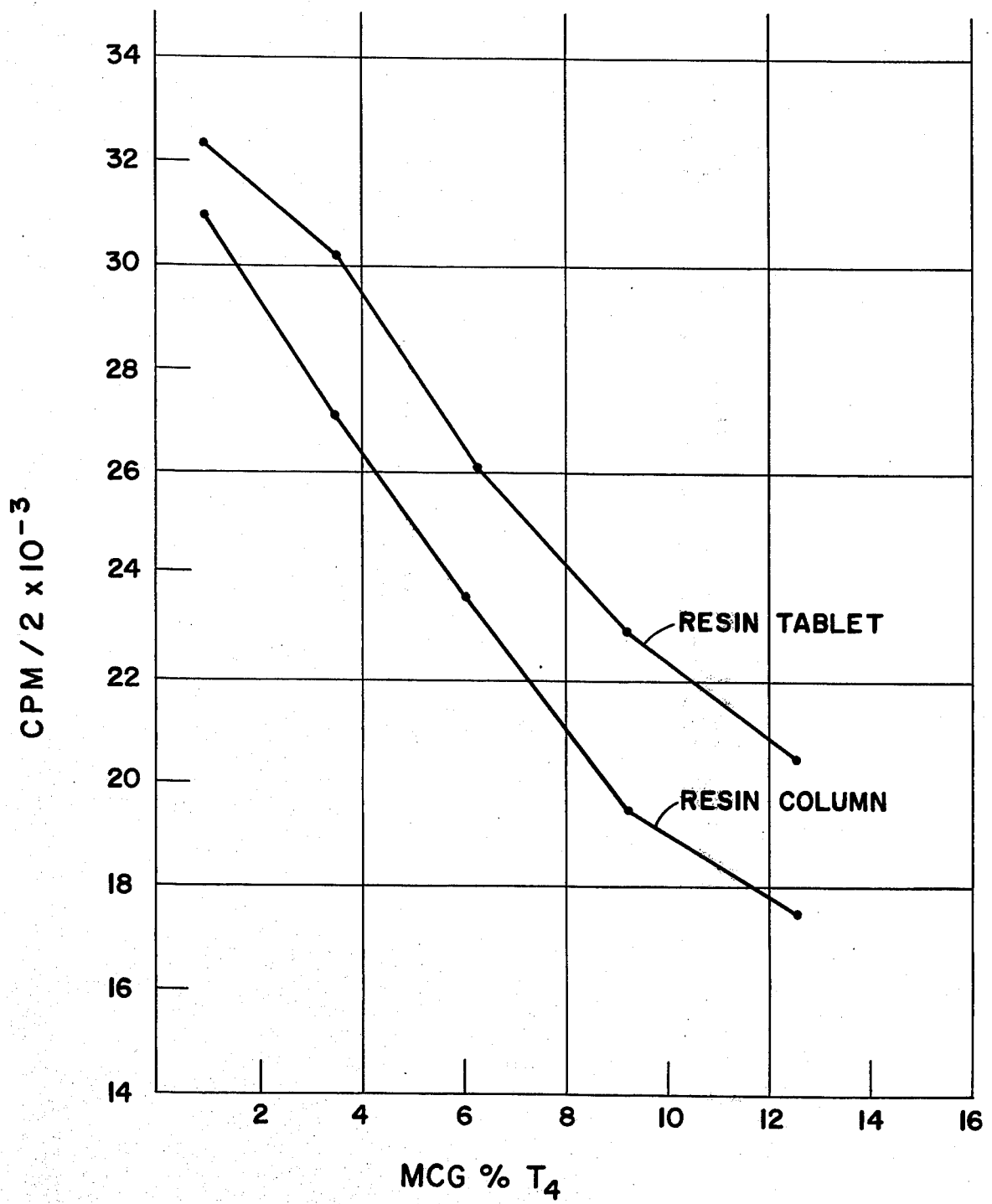
FIG_2

COMPETITIVE BINDING THYROID ASSAY WITH IMPROVED BOUND-FREE SEPARATION STEP

This invention relates to methods and materials for determining thyroid function from a blood serum sample. More particularly, it relates to a thyroid hormone assay procedure, commonly referred to as a competitive binding procedure in which the competitively bound thyroid hormone is separated from free or unbound thyroid hormone by the novel use of a certain class of resins which, in the preferred embodiment, are employed in a tablet form.

Competitive binding procedures for the assay of thyroid hormone in a serum sample are well-known in the art. Typical of the prior art is the competitive binding procedure described in U.S. Pat. No. 3,414,383 to Murphy. As described in said patent, the separation of competitively bound from free thyroid hormone has been accomplished by means of an anion exchange resin. Heretofore such resins have been strong anion exchangers, and in which the lattice upon which the functional groups are located was aromatic.

In accordance with the present invention competitive binding assays of this type are improved upon by utilizing for the bound-free separation step an intermediate base anion exchange resin. Such a resin preferably has an aliphatic lattice such as a polyalkyleneamine and has tertiary and quaternary amines thereon. For example, a resin for use in this invention may be described as one having the following structural groupings:

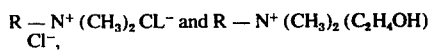

wherein R = polyalkyleneamine lattice.

In addition, resins of this type possess different non-ionic absorption, desorption characteristics due to the nonaromatic character of the lattice.

Typical of such a material is the resin commercially available from Bio-Rad Laboratories, Inc., of Richmond, Calif., and sold under the Trademark BIO-REX 5. Other useful intermediate base anion exchange resins are available, including the resin offered by Dow Chemical Company known as Dowex XFS 40396 and the resin available from Ionac Chemical Company known as IONAC-A-305. All of these resins are known as intermediate base anion exchange resins and commonly have an aliphatic lattice. The resins are to be distinguished from the strong base anion exchanges previously used and which have an aromatic lattice usually based upon polystyrene.

In the preferred embodiment the present intermediate base anion exchange resin is added to the competitive binding solution in tablet form and distributed therein preferably by mixing. Such a form has practical advantages over the column form previously utilized with the strong base anion exchange resins. The tablets are formulated so that the addition of one tablet to a test solution will constitute about 3.3–133 mg, preferably 8.3–66.7 mg for each 0.1 ml of serum in the test solution. In the preferred embodiment the intermediate base anion exchange resin is compressed with microcrystalline cellulose, preferably in a weight ratio of resin to cellulose of 1:2. The cellulose serves as a bulking and tableting agent and provides a physical form which readily breaks up when added to the competitive binding solution but which maintains physical integrity prior to such use.

In all cases the intermediate base anion exchange resin utilized generally has a wet mesh size of 50 or higher, preferably 200–400.

Apart from the utilization of an intermediate base anion exchange resin for the bound-free separation step and the utilization of such a resin in a tablet form, the present assay is consistent with prior art competitive binding procedures, including the several variations utilized for the other steps in the assay procedure. For example, the present improvement can be applied to the competitive binding procedure of the above referenced Murphy patent which includes an initial separation of thyroid hormone from serum proteins by an alcohol precipitation. Alternatives include the use of precipitation by heat or other chemical agents and, in U.S. Pat. No. 3,776,698, the use of a particulate substrate for separating thyroid hormone from its serum environment. The present invention may utilize any of these initial procedures.

A preferred procedure does not require any actual separation of thyroid hormone from its serum environment, but simply requires an inactivation of the serum associates by the addition of unbuffered acid such as hydrochloric acid. This preferred procedure is described in copending patent application Ser. No. 578,247 May 16, 1975 (said disclosure being incorporated herein by reference). All experimental procedures in the examples included herein utilize the preferred procedure of said copending application with the difference that, instead of the previously used strong base anion exchange resin columns, the instant intermediate base anion exchange resins in the preferred tablet form are employed for the bound-free separation step.

The use of intermediate base anion exchange resin is advantageous relative to the previously used strong base anion exchange resins. One indication of such advantages is in the fact that the present resins exhibit reduced stripping potential, i.e., separation of thyroid hormone which is initially bound to exogenous thyroid hormone binding protein, and thereby provides a more precise and accurate assay. To demonstrate this advantage thyroid hormone was incubated with the preferred intermediate base anion exchange resin BIO-REX 5, 100–200 wet mesh, and with a resin typical of that disclosed in U.S. Pat. No. 3,414,383, the strong base anion exchange resin BIO-RAD AG1x8 in chloride form, 200–400 wet mesh. These resins were employed in tablet form and included 75 mg of resin with 150 mg of the microcrystalline cellulose known as AVICEL. Otherwise, the competitive binding procedure of said copending application Ser. No. 578,247 was followed. Serum samples were control serum in which the serum sample designated Level I contains 0.9 mcg $T_4$/dl and Level III contains 12.3 mcg $T_4$/dl.

The procedure of said copending application, hereafter referred to by its marketed designation TETRA-COUNT II, may be briefly summarized as follows. The serum sample, either unknown or control serum, is 0.1 ml. This is added to 0.5 ml of an aqueous solution containing 0.25 M hydrochloric acid. The combined solution is mixed and incubated for 5 minutes. Thereafter, the incubated solution is combined with 3.5 ml of a competitive binding solution containing:
  a. competitive binding protein
  b. trace amount $I^{125}$
  c. 0.075 M sodium barbital, ph 8.6.

The combination is then mixed and incubated for 15 minutes. In the TETRA-COUNT II procedure the free and bound thyroid hormone are separated by pouring the solution into an anion exchange column. In the instant case an intermediate base anion exchange tablet is added to the solution and mixed by shaking for a given period of time. The solution and resin are then separated by centrifuging and decanting the supernatant, and the radioactivity of either the resin or supernatant, preferably the supernatant, is counted. In the present test, after addition of the resin tablet, the solutions were shaken for 10 and 30 seconds and percent stripping was calculated from the observed radioactivity counts after the resin and solution fractions were separated. The following table summarizes the results from the following formula which defines stripping in this context $$\% \text{ Stripping} = \frac{\text{CPM at 10 seconds} - \text{CPM at 30 seconds}}{\text{CPM at 10 seconds}} \times 100$$

(The supernatant is counted here.)

TABLE 1

| | AG 1×8 Cl⁻ 200–400 Wet Mesh % Stripping | Bio-Rex 5 100–200 Wet Mesh % Stripping | % Stripping Difference |
|---|---|---|---|
| Control Serum LEVEL I | 9.4% | 4.9% | 4.5% |
| Control Serum LEVEL III | 19.3% | 12.2% | 7.1% |

The resin employed in the present invention has been found to be superior with respect to a number of alternative resins that might have been selected. To illustrate this superior performance, the above referenced TETRA-COUNT II procedure was utilized with resin tablets for the bound-free separation. Each tablet contains 100 mg of the resins listed in Table II below. Control serums from Bio-Rad Laboratories, Inc., were used in the procedure having the concentrations shown in the Table. The counts per 30 seconds of the supernatant separated from the resin at the end of the procedure for two test repetitions are shown in the Table. Results are plotted in FIG. 1.

TABLE II

| Bio-Rad Resin | Level I 0.9 mcg T₄/dl | Level II 6.1mcg T₄/dl | Level III 12.3mcg T₄/dl |
|---|---|---|---|
| Bio-Rex 5 | 31783 | 26675 | 21409 |
| | 30968 | 26430 | 21781 |
| AG 2×4 | 37583 | 37562 | 36863 |
| | 37703 | 37469 | 36900 |
| Chelex 100 | 39172 | 37724 | 38279 |
| | 38944 | 39636 | 37845 |
| AG 3 | 34353 | 32959 | 29542 |
| | 34684 | 32854 | 30331 |
| AG 50W X4 | 38531 | 37975 | 37967 |
| | 38643 | 38117 | 37885 |
| Bio-Rex 70 | 37182 | 35901 | 35951 |
| | 37775 | 36908 | 35820 |

Thus, BIO-REX 5 resin, which is typical of the intermediate base anion exchange resins used in the present invention, exhibits a superior dose response.

Resin tablets utilized in the preferred embodiment of this invention are conveneiently made by the following procedure.

Water is removed from the selected resin such as BIO-REX 5, 200–400 wet mesh resin, using a solvent such as methanol and acetone. The resin is dried and reduced to powder form. A suitable amount of tableting agent which will provide an adequate physical integrity of the resin tablet during normal handling but which will break up easily in the aqueous competitive binding solution is blended to form a homogeneous mixture with the resin. A preferred bulking agent is microcrystalline cellulose, such as the material known by the Trademark AVICEL. It has been found that a weight ratio of resin to microcrystalline cellulose of about 1:2 provides tablets having the proper physical properties. However, other ratios can be used. The homogeneous blend of the microcrystalline cellulose is then compressed into tablets by any suitable technique. Conventional tableting machines can be used for this purpose. Tablet size is such as to provide about 3.3–133 mg of resin, preferably about 8.3–66.7 mg of resin with the balance being microcrystalline cellulose. Such tablets are convenient for use with a serum sample size of 0.1 ml.

To demonstrate the operation of the present procedure using the preferred intermediate base anion exchange resin in tablet form, the following test was carried out to provide a standard curve. For comparison, the same procedure but utilizing a strong base anion exchange resin column was conducted. The two procedures follow the TETRA-COUNT II steps as disclosed in said copending application Ser. No. 578,247 except that a tablet formulation is used in bound/free separation instead of a resin column. Thus, a novel resin in batch form replaces a strong anion resin column procedure.

1. Add resin tablets and vortex;
2. Allow the mixture to incubate at room temperature for 10 minutes; and
3. Centrifuge for 10 minutes. Count supernatant. Table III illustrates the counts observed. The results are plotted in accompanying FIG. 2.

TABLE III

| CONTROL SERUM | RESIN TABLETS Counts/30 sec. | RESIN COLUMN Counts/30 sec. |
|---|---|---|
| Bio-Rad Level I | 32000 | I 31450 |
| | 32435 | 30671 |
| M₁* | 30290 | M₁ 27192 |
| | 30333 | 27435 |
| Bio-Rad Level II | 25925 | II 23582 |
| | 26833 | 23914 |
| M₂* | 22898 | M₂ 19424 |
| | 23241 | 19797 |
| Bio-Rad Level III | 20865 | III 17907 |
| | 20576 | 17723 |
| Ortho I⁺ | 24127 | Ortho I 21421 |
| | 24020 | 22540 |
| Ortho II⁺ | 24168 | Ortho II 20381 |
| | 24213 | 20239 |
| Lederle I⁺ | 24754 | Led. I 24395 |
| | 24800 | 24453 |
| Lederle II⁺ | 25040 | Led. II 22374 |

TABLE III-continued

| CONTROL SERUM | RESIN TABLETS Counts/30 sec. | RESIN COLUMN Counts/30 sec. |
|---|---|---|
| | | 22209 |

*$M_1$ is a serum made on a 1:1 by volume mixture of Bio-Rad Levels I and II. ($M_1$ =3.5mcg $T_4$/dl)
$M_2$ is a serum made by mixing on a 1:1 by volume basis Bio-Rad Levels II and III. ($M_2$ = 9.2 mcg $T_4$/dl)
†Commercial controls The following is a summary of values obtained with the Ortho and Lederle control sera. These values fall within the range of expected results from other commercial competitive binding assays as printed on data sheets supplied by the control sera manufacturer.

TABLE IV

| | Resin Tablet Separation of Free and Bound | Expected Results of Commercial Controls |
|---|---|---|
| ORTHO I | 8.2, 8.3 ug% T-4 | 5.2–8.2mcg $T_4$/dl* |
| ORTHO II | 15.3, 15.3 ug% T-4 | 12.7–19mcg $T_4$/dl |
| LEDERLE I | 7.5, 7.5 ug% T-4 | 5.2–9.8 mcg $T_4$/dl |
| LEDERLE II | 14.1 ug% T-4 | 10–16mcg $T_4$/dl |

*Expected results were derived by radio immuno assay methodology.

The following study was made to show the precision of the improved procedure of this invention. The following data was generated by utilizing Bio-Rad control serum Level II.

TABLE V

PRECISION STUDY USING RESIN TABLET

| CPM | mcg $T_4$/dl |
|---|---|
| 26741 | 5.9 |
| 26750 | 5.8 |
| 26848 | 5.8 |
| 26554 | 6.0 |
| 26086 | 6.3 |
| 26476 | 6.0 |
| 27404 | 5.4 |
| 26842 | 5.8 |
| 26863 | 5.8 |
| 26941 | 5.8 |
| 26766 | 5.8 |
| 26939 | 5.8 |
| 27165 | 5.5 |
| 26654 | 5.9 |
| 26831 | 5.8 |
| 26396 | 6.1 |
| 26635 | 6.0 |
| 26307 | 6.2 |

Mean = 5.9 ± 0.22
Std. dev. = 0.22
c. var. - 3.7%

What is claimed is:

1. In a competitive binding assay for serum thyroid hormone having the step of separating unbound thyroid hormone from thyroid hormone bound by thyroid binding protein, the improvement comprising: separating unbound thyroid hormone by removal with an intermediate base anion exchange resin.

2. The improved competitive binding assay in accordance with claim 1, wherein said anion exchange resin has an aliphatic lattice.

3. The improved competitive binding assay in accordance with claim 2, wherein said anion exchange resin comprises tertiary and quaternary amines on a polyalkyleneamine lattice.

4. The improved competitive binding assay in accordance with claim 3, wherein the active groups in the resin include $R - N^+ (CH_3)_2 Cl^-$ and $R - N^+ (CH_3)_2 (C_2H_4OH) Cl^-$, and R = polyalkyleneamine lattice.

5. A clinical test for determining thyroid function comprising: providing a test solution containing a serum sample, treating the serum sample to render the thyroid hormone in a form suitable for competitive binding, adding a thyroid hormone radioactive tracer and exogenous thyroid hormone binding protein to form a competitive binding solution and competitively bind a portion of the test serum thyroid hormone and radioactive tracer with said exogenous thyroid binding protein, contacting said competitive binding solution with intermediate base ion exchange resin, separating said resin together with free thyroid hormone and radioactive tracer that are not bound to said exogenous thyroid binding protein, and determining the magnitude of radioactivity in at least one of (1) said exogenous thyroid hormone binding protein and (2) said ion exchange resin.

6. A test for determining thyroid function in accordance with claim 5, wherein said intermediate base anion exchange resin is in tablet form upon initial contact with said competitive binding solution and is distributed therein with mixing.

7. A test for determining thyroid function n accordance with claim 6, wherein the resin in said tablet is selected to constitute about 3.3–133 mg for each 0.1 ml of serum in the test solution.

8. A test for determining thyroid function in accordance with claim 6, wherein the resin in said tablet is selected to constitute about 8.3–66.7 mg for each 0.1 ml of serum in the test solution.

9. A test in accordance with claim 5, wherein said resin is about 50–400 wet mesh.

10. A test in accordance with claim 9, wherein the resin is about 200–400 wet mesh.

* * * * *